United States Patent

Vogt et al.

[11] 4,239,896
[45] Dec. 16, 1980

[54] 5-(OPTIONALLY SUBSTITUTED 2-AMINOPHENYL)-1H-PYRAZOLE-3-METHANOL

[75] Inventors: B. Richard Vogt, Yardley, Pa.; Ligaya M. Simpkins, Allentown, N.J.

[73] Assignee: E. R. Squibb & Sons, Inc., Princeton, N.J.

[21] Appl. No.: 86,236

[22] Filed: Oct. 18, 1979

Related U.S. Application Data

[62] Division of Ser. No. 969,642, Dec. 13, 1978, Pat. No. 4,198,412.

[51] Int. Cl.³ .......................................... C07D 231/12
[52] U.S. Cl. .................................................. 548/378
[58] Field of Search ......................................... 548/378

[56] References Cited
U.S. PATENT DOCUMENTS 3,899,508  8/1975  Wikel ..................................... 548/378
4,112,096  9/1978  Vogt ...................................... 548/378

Primary Examiner—Henry R. Jiles
Assistant Examiner—Natalia Harkaway
Attorney, Agent, or Firm—Lawrence S. Levinson; Burton Rodney

[57] ABSTRACT

Intermediates are provided having the structure

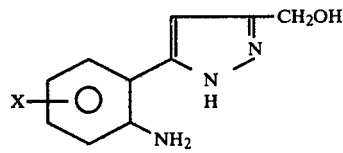

wherein X is hydrogen, lower alkyl, lower alkoxy, halogen or trifluoromethyl. These intermediates are useful in preparing pyrazolo[1,5-c]quinazoline anti-allergy compounds.

2 Claims, No Drawings

5-(OPTIONALLY SUBSTITUTED 2-AMINOPHENYL)-1H-PYRAZOLE-3-METHANOL

This is a division, of application Ser. No. 969,642, filed Dec. 13, 1978, now U.S. Pat. No. 4,198,412, issued Apr. 15, 1980.

DESCRIPTION OF THE INVENTION

The present invention relates to pyrazolo[1,5-c]quinazoline derivatives of the structure

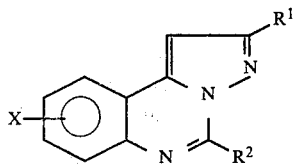

wherein $R^1$ is carboxyl; hydroxymethyl; $CO_2R^3$ wherein $R^3$ is lower alkyl, $Li^+$, $Na^+$ or $K^+$; or

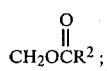
$CH_2OCR^2$;

$R^2$ is hydrogen, lower alkyl, aryl, or trifluoromethyl; and X is hydrogen, lower alkyl, lower alkoxy, halogen (Cl, Br or F) or trifluoromethyl.

Preferred are those compounds of Formula I wherein $R^1$ is carboxyl, hydroxymethyl, or lower alkoxycarbonyl, $R^2$ is hydrogen, and X is hydrogen.

Unless otherwise indicated the term "lower alkyl" or "alkyl" as employed herein includes both straight and branched chain radicals of up to eight carbon atoms, preferably up to and including 5 carbon atoms, for instance, methyl, ethyl, n-propyl, isopropyl, n-butyl, t-butyl, isobutyl, n-pentyl, n-hexyl, isohexyl, n-heptyl, 4,4-dimethylpentyl, n-octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(-lower alkyl)phenyl (e.g., 2,4-dimethylphenyl, 3,5-diethylphenyl, and the like), halophenyl (e.g., chlorophenyl, bromophenyl, iodophenyl, fluorophenyl).

The compounds of Formula I of the invention may be prepared by several methods.

One method involves preparation of compounds of the structure

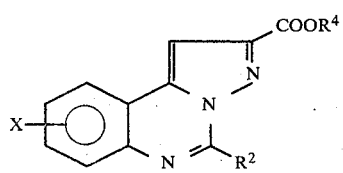

wherein $R^4$ is hydrogen or lower alkyl, and X and $R^2$ are as defined hereinbefore. The Formula II compounds are prepared by reacting compounds of the structure

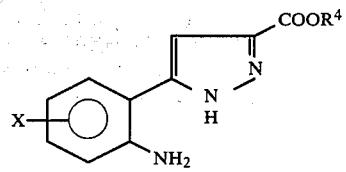

with an acylating agent which may be an aliphatic carboxylic acid of the structure

$R^2COOH$      IV or aliphatic carboxylic acid halide of the structure

$R^2COHal$      V wherein Hal is Cl or Br, or an aliphatic acid anhydride of the structure

$(R^2CO)_2O$      VI or mixtures of any or all of the above (IV, V and/or VI), at a temperature within the range of from about $-30°$ C. to about 350° C., preferably from about 0° C. to about 250° C., for periods of 0.5 to 48 hours.

The Formula III compounds may be prepared as described in U.S. Pat. No. 3,899,508.

Compounds of Formula I wherein $R^1$ is

$CH_2OCR^2$ may be prepared by reacting a 5-(optionally substituted 2-aminophenyl)-1H-pyrazole-3-methanol, that is

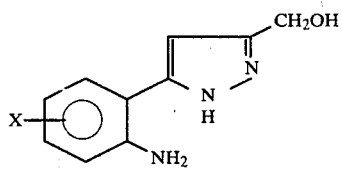

or a salt thereof, with an aryl or aliphatic carboxylic acic of the structure

$R^2COOH$      VIII at a temperature within the range of from about 0° to about 320° C., and preferably from about 25° to 260° C. for periods of 0.5 to 48 hours.

The Formula VII compound may be prepared by reducing an alkyl ester of 5-(optionally substituted 2-aminophenyl)-1H-pyrazole-3-carboxylic acid (prepared as described in U.S. Pat. No. 3,899,508) with a reducing agent such as lithium borohydride ($LiBH_4$) in an inert solvent such as tetrahydrofuran.

Compounds of Formula I wherein $R^1$ is hydroxymethyl may be prepared by acid or base hydrolysis of compounds of Formula I wherein $R^1$ is

Compounds of Formula I in the form of $Li^+$, $Na^+$ or $K^+$ salts, that is $R^1$ is $COO^{\ominus}Li^{\oplus}$, $COO^{\ominus}Na^{\oplus}$ or $COO^{\ominus}K^{\oplus}$ may be prepared by neutralizing a pyrazolo[1,5-c]quinazoline-2-carboxylic acid of the invention, that is

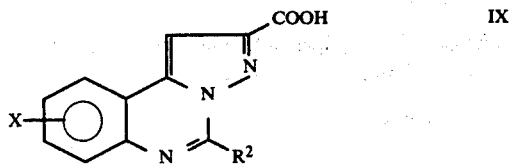

with an appropriate lithium, sodium or potassium salt, such as sodium or potassium carbonate or sodium or potassium hydroxide.

The compounds of Formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of Formula I, and the pharmaceutically acceptable salts thereof, are orally active as anti-allergics and inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats and inhibition of histamine release from mast cells. See Bach, Immediate Hypersensitivity: Laboratory Models and Experimental Findings, Ann. Rep. Med. Chem., 7:238-248 (1972), for a discussion of the predictability of clinical efficacy of compounds active in the PCA. In addition anti-allergy activity of these compounds is determined by inhibition of histamine release from mast cells according to a modified procedure based on the procedure described by L. G. Garland et al, British Journal of Pharmacology, Vol. 50, p. 137 (1974).

A compound of Formula I, or a salt thereof, can be administered by the inhalation of an aerosol or powder as described in U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

The letter "(d)" following a melting point indicates at least some apparent decomposition was observed. The term "stripped" also means evaporation.

EXAMPLE 1

Pyrazolo[1,5-c]quinazoline-2-carboxylic acid 3.0 g (0.0148 mole) of 5-(2-aminophenyl)-1H-pyrazole-3-carboxylic acid is suspended in 21 ml of 97+% HCOOH, and the reaction mixture heated in an oil bath at 100° for 2 hours. The reaction mixture is cooled, diluted with water (75 ml), stirred for 30 minutes and filtered, washing the precipitates well with water. The crude product is dried overnight in vacuo at 90°. Yield: 2.9 g. Percent crude yield: 91.8%.

The crude product is taken up in dioxane (300 ml), treated with activated carbon while boiling for 10-15 minutes and filtered through a celite pad. The pad is washed with small amounts of dioxane and methanol, the washings combined with the filtrate and the clear solution concentrated down to a volume of 125 ml. The solution is then cooled and the precipitates that form are filtered off and dried overnight in vacuo at 90°. Yield: 1.86 g., m.p. 284°-285°.

EXAMPLE 2

Pyrazolo[1,5-c]quinazoline-2-carboxylic acid, sodium salt 1.0 g (0.0047 mole) of pyrazolo[1,5-c]-quinazoline-2-carboxylic acid (prepared as described in Example 1) is suspended in 100 ml of water, treated with 394 mg (1 eq) of sodium bicarbonate and stirred overnight at room temperature. The reaction mixture is filtered and the clear filtrate is treated with activated carbon, heated on a steam bath for 10 minutes and filtered through a celite pad, washing the pad well with water. The washings and filtrate are combined and stripped to dryness. Yield: 0.9 g. Percent crude yield=81.45%.

The crude product is triturated with 12 ml of 50% aqueous methanol and filtered, washing the white precipitate with a small amount of 50% aqueous methanol. The product is then dried overnight in vacuo at 100°. Yield: 0.72 g, m.p. 400°.

EXAMPLE 3

Pyrazolo[1,5-c]quinazoline-2-carboxylic acid, methyl ester 10.0 g (0.046 mole) of the methyl ester of 5-(2-aminophenyl)-1H-pyrazole-3-carboxylic acid is suspended in 70 ml of 97+% formic acid and heated at 100° for 2 hours. The reaction mixture is cooled, diluted with water (250 ml) and stirred for 10–15 minutes. The precipitates are filtered off and washed well with water. The solid is then taken up in chloroform (500 ml), the residual water layer separated and the organic layer dried over anhydrous sodium sulfate. The organic phase is filtered and the clear filtrate stripped to dryness. Yield: 10.0 g; 96% crude yield (theoretical yield=10.41 g).

The crude product is taken up in 1.25 liter of benzene and the resulting clear solution concentrated down to a volume of 200 ml. The needle-shaped crystals are filtered off and dried for 48 hours in vacuo at 55°. Yield: 9.22 g, m.p. 181°–183°.

EXAMPLE 4

5-Methylpyrazolo[1,5-c]quinazoline-2-carboxylic acid, methyl ester 1.5 g (0.0069 mole) of the methyl ester of 5-(2-aminophenyl)-1H-pyrazole-3-carboxylic acid is dissolved in a mixture of 20 ml of glacial acetic acid and 1.56 ml of acetyl chloride and stirred overnight at room temperature. The solvent is stripped off and the slurry poured onto 200 ml ice-water and stirred for 30 minutes. The precipitates that form (~800 mg) are filtered off and air dried. These are then taken up in 30 ml of benzene, filtered while hot and the clear filtrate concentrated down to a volume of 10 ml and cooled. The product is filtered off and dried overnight in vacuo at room temperature. Yield: 500 mg, m.p. 155°–156° C.

EXAMPLE 5

5-(Trifluoromethyl)pyrazolo[1,5-c]quinazoline-2-carboxylic acid, methyl ester 500 mg (0.0023 mole) of the methyl ester of 5-(2-aminophenyl)-1H-pyrazole-3-carboxylic acid is taken up in 10 ml of trifluoroacetic anhydride and refluxed for 3 hours. (Precipitates start to come out of solution within the first 30 minutes). The reaction mixture is stripped to dryness and the solids obtained are evaporated twice from benzene.

The crude product (~700 mg) is recrystallized from benzene (10 ml) and dried overnight in vacuo at 60°. Yield: 305 mg, m.p. 209°–211°.

EXAMPLE 6

5-Phenylpyrazolo[1,5-c]quinazoline-2-carboxylic acid, methyl ester 500 mg (0.0023 mole) of the methyl ester of 5-(2-aminophenyl)-1H-pyrazole-3-carboxylic acid and 5.2 g (0.023 mole) of benzoic anhydride are heated together at 255° for 1 hour and at 150° for 5 hours. The reaction mixture is cooled and the resulting solid taken up in 40 ml of water and treated portionwise with sodium bicarbonate. The aqueous solution is layered with 50 ml of methylene chloride and stirred for 30 minutes. The organic layer is then separated, dried over anhydrous sodium sulfate and chromatographed on a silica gel column (15 g), eluting the column successively with $CH_2Cl_2$ (25 ml), $CH_2Cl_2$:EtOAc (8:2; 75 ml) and $CH_2Cl_2$:EtOAc (1:1; 70 ml).

All the fractions containing the product are combined and stripped to dryness. The light brown solid is triturated with 20 ml of ether, filtered and dried overnight in vacuo at 60°. Yield: 658 mg, m.p. 205°–206°. The crude product is taken up in benzene (50 ml), filtered while hot and the clear filtrate concentrated down to a volume of 20 ml and cooled. The needle-shaped precipitates are filtered off, washed with a small amount of ether and dried overnight in vacuo at 80°. Yield: 423.4 mg, m.p. 201°–203°.

EXAMPLE 7

Pyrazolo[1,5-c]quinazoline-2-methanol, formate ester

A. 5-(2-Aminophenyl)-1H-pyrazole-3-methanol, hydrochloride 2.0 g (0.0092 mole) of the methyl ester of 5-(2-aminophenyl)-1H-pyrazole-3-carboxylic acid and 420 mg of 95% $LiBH_4$ are stirred together in 48 ml of distilled tetrahydrofuran at room temperature for 36 hours. The reaction mixture is cooled down to 0°, acidified dropwise with 20 ml of 1 N HCl and stirred for 30 minutes. The acidic suspension is diluted with water (40 ml), stirred for another 15 minutes and stripped to dryness. The resulting solid is taken up in absolute ethanol and filtered through florisil in a sintered glass funnel, washing the florisil with absolute ethanol (50 ml).

The light yellow filtrate is concentrated down to a syrup which is dissolved in 50 ml of absolute ethanol and treated with 2.9 ml ($\cong$1.1 equivalent) of 4 N $Et_2O$/HCl and stirred for 30 minutes. The resulting suspension is diluted further with ether (50 ml), stirred for 10 minutes and filtered. The precipitates are washed well with ether and dried overnight in vacuo at 60°. Yield: 2.2 g, m.p. 217°–218°.

1.2 g of the crude hydrochloride is taken up in hot absolute ethanol (40 ml), filtered while hot and the clear filtrate concentrated down to a volume of ~10 ml. After cooling, the cream-colored precipitates are filtered off and dried overnight in vacuo at 80°. Yield: 810 mg, m.p. 220°–222°.

B. Pyrazolo[1,5-c]quinazoline-2-methanol, formate ester 4.0 g (0.0176 mole) of crude 5-(2-aminophenyl)-1H-pyrazole-3-methanol hydrochloride and 28 ml of 97+% HCOOH are heated at 100° for 5 hours. The reaction mixture is cooled, stripped to dryness and the resulting solid stirred with water (50 ml) for 30 minutes. The fluffy white precipitates that form are filtered off and air dried. Yield: 3.5 g; 2 major spots on TLC. Percent yield (crude): 87.7% (theoretical yield=3.99 g).

The crude product is suspended in methylene chloride (30 ml) and chromatographed on a silica gel column (50 g; 1"×11"), eluting the column successively with $CH_2Cl_2$ (50 ml), $CH_2Cl_2$:EtOAc (8:2; 100 ml), $CH_2Cl_2$:EtOAc (1:1; 420 ml) and EtOAc (200 ml). The desired fractions are combined to give 2.87 g of the product. The product from the column is taken up in benzene (100 ml), the solution filtered while hot, and the clear filtrate concentrated down to a volume of ~30 ml and cooled. The fluffy white precipitates are filtered off and dried overnight in vacuo at 50°. Yield: 2.35 g, m.p. 118°–120°.

EXAMPLE 8

Pyrazolo[1,5-c]quinazoline-2-methanol 880 mg (0.0039 mole) of the formate ester of pyrazolo[1,5-c]quinazoline-2-methanol (prepared in Example 7) is suspended in 42.2 ml of 0.1 N NaOH and stirred at room temperature for 30 minutes. The precipitates are filtered off, washed with a small amount of water and air dried. The crude product (1.09) is taken up in ethyl acetate (60 ml), filtered while hot and the clear filtrate is concentrated down to a volume of ~25 ml and cooled. The needle-shaped precipitates are filtered off, air dried and combined with a previous batch, (374.9 mg). The product is then pulverized and the powder obtained dried overnight in vacuo at 60°. Yield: 1.10 g, m.p. 132°–133°.

EXAMPLES 9 to 17

Following the procedure of Example 1 but substituting the starting material indicated in Column I of Table I set out below for the 5-(2-aminophenyl)-1H-pyrazole-3-carboxylic acid, the products indicated in Column II are obtained.

TABLE I

| Ex. No. | Column I — X (position) | Column II — X (position) |
|---|---|---|
| 9. | $CH_3(5)$ | $CH_3(9)$ |
| 10. | $CH_3(4)$ | $CH_3(8)$ |
| 11. | Cl(3) | Cl(7) |
| 12. | Br(4) | Br(8) |
| 13. | F(4) | F(8) |
| 14. | $CF_3(5)$ | $CF_3(9)$ |
| 15. | Cl(6) | Cl(10) |
| 16. | $CH_3O(6)$ | $CH_3O(10)$ |
| 17. | $CH_3O(5)$ | $CH_3O(9)$ |

EXAMPLES 18 to 26

Following the procedure of Example 2, but substituting the compounds of Examples 9 to 17 for pyrazolo[1,5-c]quinazoline-2-carboxylic acid, the sodium salts of the compounds of Examples 9 to 17 are obtained.

EXAMPLES 27 to 36

Following the procedure of Examples 3 to 6, but substituting for the methyl ester of 5-(2-aminophenyl)-1H-pyrazole-3-carboxylic acid, the compound set out in Column I of Table II below and substituting for the acylating agent in Examples 3 to 6, the acylating cyclizing agent shown in Column II, the product shown in Column III is obtained.

TABLE II

| Ex. No. | Column I X(position) | Column I $R^4$ | Column II (Acylating Agent) (1) $R^2COOH$ (2) $(R^2CO)_2O$ (3) $R^2COHal$ | Column III X(position) | Column III $R^4$ | Column III $R^2$ |
|---|---|---|---|---|---|---|
| 27. | H | H | (1) $CH_3COOH$ | H | | |
| 28. | H | $C_2H_5$ | (1) HCOOH | H | as per Column I | as per Column II |
| 29. | H | $CH_3$ | (1) $C_2H_5COOH$ (3) $C_2H_5COCl$ | H | | |
| 30. | $CH_3(5)$ | $C_2H_5$ | (1) $CH_3COOH$ (3) $CH_3COCl$ | $CH_3(9)$ | | |

TABLE II-continued

| | Column I | | Column II | Column III | | |
|---|---|---|---|---|---|---|
| | (structure with COOR⁴, NH, NH₂) | | (Acylating Agent)<br>(1) R²COOH<br>(2) (R²CO)₂O<br>(3) R²COHal | (structure with COOR⁴, N-R²) | | |
| Ex. No. | X(position) | R⁴ | | X(position) | R⁴ | R² |
| 31. | CH₃O(6) | CH₃ | (2) (CF₃CO)₂O | CH₃O(10) | | |
| 32. | Cl(4) | C₃H₇ | (2) (CF₃CO)₂O | Cl(8) | | |
| 33. | Br(5) | C₂H₅ | (2) (C₆H₅CO)₂O | Br(9) | | |
| 34. | F(3) | CH₃ | (2) (C₆H₅CO)₂O | F(7) | as per | as per |
| 35. | CF₃(5) | H | (1) HCOOH | CF₃(9) | Column I | Column II |
| 36. | H | CH₃ | (2) (C₆H₅CO)₂ | H | | |

EXAMPLES 37 to 45

Following the procedure of Example 7, parts A and B, except substituting for the methyl ester of 5-(2-aminophenyl)-1H-pyrazole-3-carboxylic acid, the starting material shown in Column I of Table III below, and substituting for formic acid, the acylating agent shown in Column II, the product shown in Column III is obtained.

TABLE III

| | Column I | | Column II | Column III | |
|---|---|---|---|---|---|
| | (structure with C(O)-OR⁴, NH, NH₂) | | R²COOH | (structure with CH₂OCR², N-R²) | |
| Ex. No. | X(position) | R⁴ | R² | X(position) | R² |
| 37. | CH₃(5) | C₂H₅ | H | CH₃(9) | |
| 38. | CH₃(4) | CH₃ | C₂H₅ | CH₃(8) | as per |
| 39. | Cl(3) | CH₃ | CF₃ | Cl(7) | Column II |
| 40. | Br(4) | C₃H₇ | C₆H₅ | Br(8) | |
| 41. | F(4) | C₂H₅ | CH₃ | F(8) | |
| 42. | CF₃(5) | CH₃ | CF₃ | CF₃(9) | |
| 43. | Cl(6) | C₃H₇ | H | Cl(10) | |
| 44. | CH₃O(6) | CH₃ | H | CH₃O(10) | |
| 45. | CH₃O(5) | C₄H₉ | C₂H₅ | CH₃O(9) | |

EXAMPLES 46 to 54

Following the procedure of Example 8, except substituting for the formate ester of pyrazolo-[1,5-c]quinazoline-2-methanol, the ester shown in Examples 37 to 45, the corresponding pyrazolo-[1,5-c]quinazoline-2-methanol is obtained.

What is claimed is:

1. A compound of the formula (structure showing substituted phenyl with X, NH₂, connected to pyrazole ring with CH₂OH group)

wherein X is hydrogen, lower alkyl, lower alkoxy, halogen or trifluoromethyl.

2. The compound of claim 1 wherein X is hydrogen.

* * * * *

UNITED STATES PATENT AND TRADEMARK OFFICE
CERTIFICATE OF CORRECTION

PATENT NO. : 4,239,896
DATED : December 16, 1980
INVENTOR(S) : B. Richard Vogt et al.

It is certified that error appears in the above-identified patent and that said Letters Patent are hereby corrected as shown below:

Column 2, line 52, "acic" should read --acid--.

Column 3, line 7, "COO$^{\ominus}$Li$^{\ominus}$" should read --COO$^{\ominus}$Li$^{\oplus}$--.

Column 8, Table I, Column II, the structure in the column heading should read

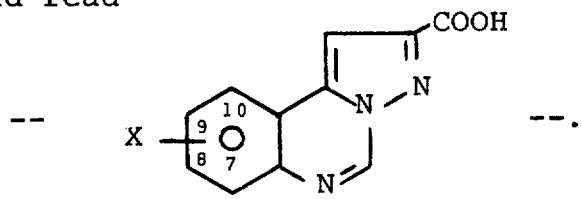

Column 8, Table II, Column III, the structure in the column heading should read

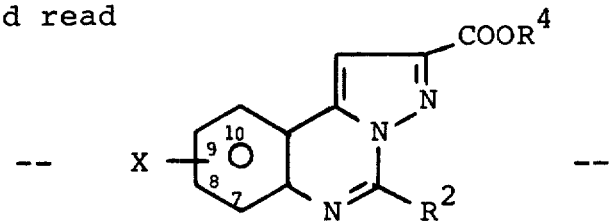

Signed and Sealed this

Twenty-fourth Day of March 1981

[SEAL]

Attest:

RENE D. TEGTMEYER

Attesting Officer

Acting Commissioner of Patents and Trademarks